United States Patent
Kramer et al.

(10) Patent No.: US 8,073,204 B2
(45) Date of Patent: Dec. 6, 2011

(54) HYBRID MULTI-SENSOR BIOMETRIC IDENTIFICATION DEVICE

(75) Inventors: Alan Kramer, Berkeley, CA (US); Giovanni Gozzini, Berkeley, CA (US)

(73) Assignee: Authentec, Inc., Melbourne, FL (US)

( * ) Notice: Subject to any disclaimer, the term of this patent is extended or adjusted under 35 U.S.C. 154(b) by 1011 days.

(21) Appl. No.: 11/967,883

(22) Filed: Dec. 31, 2007

(65) Prior Publication Data
US 2009/0166411 A1 Jul. 2, 2009

(51) Int. Cl.
*G06K 9/00* (2006.01)
*G05B 19/00* (2006.01)

(52) U.S. Cl. ....... 382/115; 382/124; 382/312; 340/5.52; 250/208.1

(58) Field of Classification Search .......... 382/124, 382/127, 126, 312, 115; 340/5.53, 5.52; 250/200, 206, 555, 556, 216, 229, 227.11, 250/208.1, 221; 356/71; 345/165, 167, 166; 235/380; 361/283.1
See application file for complete search history.

(56) References Cited

U.S. PATENT DOCUMENTS

| | | | |
|---|---|---|---|
| 5,844,287 A | 12/1998 | Hassan et al. | |
| 5,864,296 A | 1/1999 | Upton | |
| 5,942,761 A | 8/1999 | Tuli | |
| 6,028,773 A * | 2/2000 | Hundt | 361/760 |
| 6,097,035 A | 8/2000 | Belongie et al. | |
| 6,980,286 B1 | 12/2005 | Feng | |
| 7,147,153 B2 | 12/2006 | Rowe et al. | |
| 7,274,808 B2 * | 9/2007 | Baharav et al. | 382/124 |
| 7,321,701 B2 * | 1/2008 | Setlak et al. | 382/312 |
| 7,358,515 B2 * | 4/2008 | Setlak et al. | 250/556 |
| 7,361,919 B2 * | 4/2008 | Setlak | 250/556 |
| 7,403,644 B2 * | 7/2008 | Bohn et al. | 382/126 |
| 7,619,194 B2 * | 11/2009 | Kobashi | 250/205 |
| 2004/0213440 A1 | 10/2004 | Joo et al. | |
| 2005/0069181 A1 | 3/2005 | Setlak et al. | |

FOREIGN PATENT DOCUMENTS

| | | |
|---|---|---|
| EP | 08 10 5955 | 3/2009 |
| WO | WO99/28701 A | 6/1999 |
| WO | WO2004/066693 A | 8/2004 |

OTHER PUBLICATIONS

Rowe, Robert K., "A Multispectral Sensor for Fingerprint Spoof Detection", Sensors, vol. 22, No. 1, (Jan. 2005), pp. 2-4.

* cited by examiner

*Primary Examiner* — Sheela Chawan
(74) *Attorney, Agent, or Firm* — Allen, Dyer, Doppelt, Milbrath & Gilchrist, P.A.

(57) ABSTRACT

An improved fingerprint sensing device is provided with multiple sensing apparatus, two or more of which operating on different sensing principles. For example, a capacitive sensor may be integrally formed with an optical sensor on a single substrate. Ideally, the multiple sensing apparatus are disposed such that they may sense nearly identical portions of a fingerprint simultaneously. A primary sensor may be employed to establish the identity of a user based on a fingerprint, while a secondary sensor may be employed to establish that the fingerprint is part of a live human (anti-spoofing). Integrated light sources may be provided to drive an optical sensor. The light sources may also provide visual cues for usage, and enhance the aesthetics of the device.

8 Claims, 6 Drawing Sheets

HYBRID MULTI-SENSOR BIOMETRIC IDENTIFICATION DEVICE

BACKGROUND OF THE INVENTION

1. Field of the Invention

The present invention is related to devices for biometric identification, and more specifically to an integrated multi-sensor device, such as a hybrid optical and electronic sensor, which may be employed for biometric identification, authentication, etc.

2. Description of the Prior Art

It is well known that no two person's fingerprints are identical. The differences between two individuals' fingerprints can therefore be used to identify and distinguish individuals for a variety of applications. Two primary categories of fingerprint sensing technology exist today: electrical and optical.

Broadly, optical sensing uses light (visible or otherwise) to capture an image of a user's fingerprint. For example, if a sufficiently intense light is incident on a user's finger, some of that light will be reflected. This reflection may be captured as an image and compared to a reference image to establish the identity of the user. There are many variations on this basic optical technology, including the selection of one or more different wavelengths of light to image the fingerprint, direct imaging, scanned imaging, total internal reflection (TIR) imaging, image enhancement (e.g., polarization), etc. In order to address difficulties such as dry, dirty or thickly callused skin, or fingertips worn smooth or damaged by surface cuts, scrapes, etc. which interfere with simply observing the surface pattern of an individual's fingerprints, certain optical fingerprint sensors examine attributes of a user's finger below the surface of the skin. See, e.g., Rowe et al., U.S. Pat. No. 6,560,352, which is incorporated by reference herein. Fundamentally, however, all optical technologies operate by capturing an image of a portion of a user's finger using light emitted from a light source.

Again broadly, electrical sensing captures an image of a user's fingerprint by measuring the response of one or more electrical components in the presence of the fingerprint. These responses are examined to determine characteristics of the surface and/or structure of a user's skin at or proximate the tip of the user's finger which are indicative of a fingerprint pattern. For example, capacitance is in part a function of the distance between two electrodes. If one electrode is a plate in the sensor and the other is a portion of a user's finger, as the distance between the finger and the plate vary the capacitance will vary. According to another example, the presence of a finger can alter the fringing effect between the two capacitor plates in a substrate. In either case, the height differences between a ridge and a valley (relative to the plate) in a fingerprint can be determined by observing the change in capacitance. An image of the fingerprint (or equivalently, regions thereof) can then be constructed. See e.g., Kramer, U.S. Pat. No. 6,512,381; Tartagni, U.S. Pat. No. 6,320,394; Knapp, U.S. Pat. No. 5,325,442; Tamori, U.S. Pat. No. 5,400,662; and Tamori, U.S. Pat. No. 5,429,006; each of which being incorporated by reference herein.

As each of the various optical and electrical sensing technologies have, to a greater or lesser extent, disadvantages which lead to errors in image construction and ultimately the possibility of misidentification a user, there is a virtually unending need to improve the accuracy of biometric sensing and identification. Furthermore, while no two individuals will have identical fingerprints, it is possible to construct a replica of an individual's fingerprint using a latent print or other captured form of an original fingerprint. Such replicated prints have historically been used to defeat the security of biometric identification systems, (so-called "spoofing"). Techniques for defeating spoofing, such as measuring temperature, electrical conductivity, optical reflectivity, etc. of the finger and proximate tissue are known (and referred to as "anti-spoofing"). However, virtually as soon as a new anti-spoofing technique is deployed, an effort surfaces to defeat it. Therefore, in addition to improved accuracy, there is a continuous need to improve anti-spoofing techniques.

SUMMARY OF THE INVENTION

Accordingly, the present invention is directed to a sensor architecture employing a combination of sensing technologies integrated into a single apparatus to provide improved biometric sensing. While the particular technologies (e.g., optical and electrical) employed by the sensor of the present invention may vary, the two technologies are disposed to work in parallel to optimize the accuracy and security of the fingerprint sensing.

As used in the following, "fingerprint" shall mean not only the unique pattern of ridges and valleys present on a surface of a human user's finger, but shall also include the unique biometric characteristics such as density, temperature, resistivity, structural assembly, etc. associated with that portion of a user (which need not necessarily be a finger) being used to identify that user. "Sensor" shall mean any device capable of detecting those unique biometric characteristics being used to identify that user. Components which are "disposed integrally" are components ultimately located in a single, unitary body structure or enclosure, for example as a part of the formation of that body structure. Two sensors are said to "operate on different principles" when those sensors function to sense biometric attributes according to different phenomena or processes. "Substrate" shall mean a single body structure, such as a crystalline (e.g., silicon) body to which lithography, deposition, and other processing steps may be applied. "Carrier body" shall mean a carrier structure for rigidly holding one or more components, such as a body of bulk molding material formed to encase one or more previously formed electrical and/or optical components, etc. Other terms used throughout this disclosure shall have their ordinary and broadest meaning unless specifically defined otherwise herein.

According to one aspect of the invention, an optical sensor (and optionally an associated light source) is disposed integrally in an enclosure with an electrical sensor structure. The optical and electrical sensors are disposed in close proximity to one another so as to simultaneously sense, as closely as practicable, the same region of a fingerprint.

According to another aspect of the present invention in which an optical sensor and light source are disposed integrally in an enclosure with an electrical sensor structure, a sensor enclosure is comprised of a material, such as an appropriate plastic, which is transmissive at the wavelength(s) of light emitted by the light source. The enclosure material serves to mechanically hold the elements in their respective positions and provide durability and protection for those elements while permitting the sensor to sense light emitted by the light source through said enclosure material.

According to yet another aspect of the present invention in which an optical sensor and light source are disposed integrally in an enclosure with an electrical sensor structure, the light source is polychromatic and the optical sensor capable of selectively sensing the various wavelengths emitted by the light source. The various wavelengths of the light source are absorbed or reflected by different layers of the finger being sensed, providing an image of those various layers.

According to still another aspect of the present invention in which an optical sensor and light source are disposed integrally in an enclosure with an electrical sensor structure, the light source emits at one or more wavelengths visible to a user. The user may thus be provided cues to use of the sensor and feedback regarding successful or unsuccessful operation of the sensor. The sensor may also be provided with a visual uniqueness to enhance marketing and permit distinguishing the source of the sensor from other manufacturers or products.

While according to certain aspects of the present invention the optical and electrical sensors are integrally formed in a single, common substrate, according to a still further aspect of the present invention, the optical and electrical sensors are discrete elements, such as portions of separate sub-systems, assembled as a single apparatus. Preferably, the sensing devices are in close proximity to one another, and operate in parallel to provide enhanced fingerprint sensing and identification. Indeed, the two may be so close as to effectively be part of the same pixel. If not formed in a single substrate, the discrete sensing devices may be carried by a unitary carrier body, such as a molded structure, to maintain their relative positions.

According to yet another aspect of the invention, two or more sensors, each of a type such that the sensing function of one does not interfere with the sensing function of the other, are disposed such that they are capable of sensing the same regions of a user's fingerprint. Through their relative positions or software within a processing system or both, the two sensors are capable of nearly simultaneously sensing that region of the fingerprint. The sensor combinations may be, for example, optical/electrical, electrical/electrical or another appropriate hybrid combination. Each sensor of the sensor combination may have the same resolution or may have different resolutions. That is, one sensor type, for example optical, may have a lower resolution than another sensor type, for example capacitive. The choice of sensor type, size, position, resolution, etc. will depend on the application, the intended function for each sensor type, and many other factors as will be appreciated by one skilled in the art given the present disclosure.

The above is a summary of a number of the unique aspects, features, and advantages of the present invention. However, this summary is not exhaustive. Thus, these and other aspects, features, and advantages of the present invention will become more apparent from the following detailed description and the appended drawings, when considered in light of the claims provided herein.

BRIEF DESCRIPTION OF THE DRAWINGS

In the drawings appended hereto like reference numerals denote like elements between the various drawings. While illustrative, the drawings are not drawn to scale. In the drawings.

DETAILED DESCRIPTION OF THE INVENTION

Figure 1:
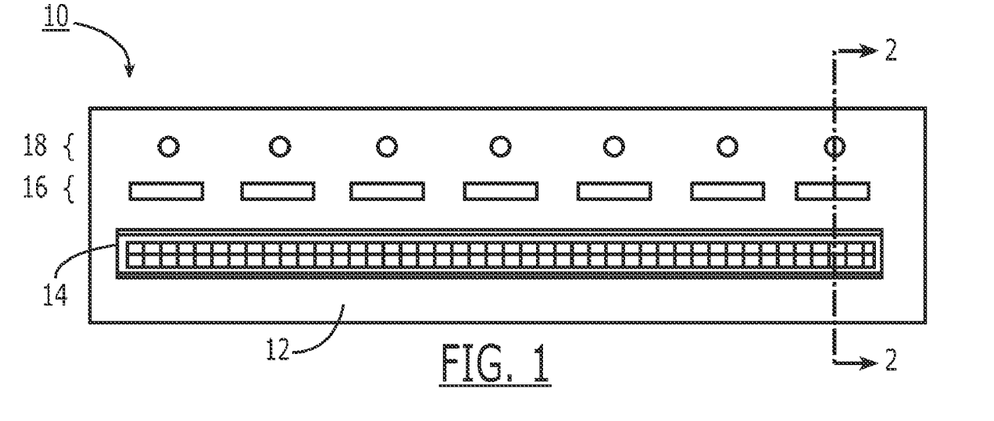
FIG. 1 is a plan view of a hybrid electrical/optical fingerprint sensor structure according to one embodiment of the present invention.

With reference to FIG. 1, a first embodiment 10 of a hybrid multi-sensor biometric identification device according to the present invention is illustrated. FIG. 1 is a top view of the device consisting of: a unitary body structure 12 having disposed therein an electrical sensor array 14, an optical sensor array 16, and a light source array 18, each described in further detail below. While the embodiment shown in FIG. 1 illustrates the basic principles of the invention, the specific arrangement of devices (e.g., relative placement, number of elements, etc.) is not critical to the broad concept of a hybrid electrical/optical fingerprint sensor according to the present invention.

According to one embodiment, body structure 12 will typically be a plastic, phenolic, acrylic, glass, or similar material providing mechanical support and protection for various elements placed or formed therein. The material may be fully or partially transmissive or opaque, depending on the arrangement of elements therein, as described further below. According to such an embodiment, body 12 is a transmissive phenolic-based structure slightly wider than the width of an average fingerprint, for example on the order of between 1 and 2 cm (e.g., perpendicular to the direction of motion of a finger when reading a fingerprint), and a relatively smaller length, for example on the order of between 3 and 5 mm (e.g., in the direction of motion of a finger when reading a fingerprint), although many other dimensional choices are available, and these dimensions are not limitations on the nature and scope of the present invention.

In one variation of this embodiment, electrical sensor array 14, optical sensor array 16, and light source array 18, are independently fabricated. In another variation of this embodiment, two or more of these elements, such as electrical sensor array 14 and optical sensor array 16, are formed together using similar processing steps (e.g., on a single, silicon substrate using similar deposition, lithography, and other processing steps). In either variation, these elements are then positioned within a molding device, and body structure 12 formed therearound by, for example, a molding process well known in the art to form an integral structure. Electrical interconnections may be surface mounted or through body structure 12 as may be appropriate for the application of the hybrid multi-sensor device according to the present invention.

As mentioned, disposed within body structure 12 is electrical sensor array 14 which, according to one embodiment, is an array of capacitive fingerprint sensor cells, for example as disclosed in U.S. Pat. No. 6,114,862 or U.S. Pat. No. 6,927,581 (each of which being incorporated by reference herein) and arranged to capture multiple portions of a fingerprint, for example as disclosed in U.S. Pat. No. 6,580,816 (which is also incorporated by reference herein). Preferably, electrical sensor array 14 will be several (e.g., two) rows of essentially 1-dimensional sensor arrays physically abutting one another across which a user swipes a finger. Such arrays typically capture images of multiple portions of a user's fingerprint, with the complete print being assembled by software or hardware associated with the sensor system. One advantage of such an arrangement is a relatively compact size, allowing for the inclusion of additional elements within body structure 12 proximate the sensor arrays.

While capacitive sensor systems are generally effective to capture images of most fingerprints, the greater the accuracy of the captured fingerprint the greater the security which may be provided. In addition, while sensing a fingerprint is a crucial task for such a system, there is also a need to recognize and block attempts to perpetrate fraud on such a system. For example, a capable fingerprint recognition system should be able to distinguish a live finger from a synthetic finger. With respect to these aspects of fingerprint sensing, we have determined that great benefit may be obtained when a secondary sensing system is employed in conjunction with an electronic sensing system.

Ideally, when using two sensing systems in conjunction with one another, the two systems would sense the exact same portions of a fingerprint at the exact same time. The results of each could be compared, additional data derived, etc. to obtain an image, identify an associated identity, identify attempted fraud, etc. However, due to the physical sizes and placement of sensing elements, it is not possible to truly sense identical portions of a fingerprint simultaneously by two distinct sensors. However, using the aforementioned 1-dimensional arrays, a compact electronic sensor array 14 is provided, allowing the formation or placement of secondary sensing elements in close proximity to array 14, spaced apart for example on the order of a fraction of a millimeter. This close spacing permits sensing nearly-identical portions of the fingerprint simultaneously, approaching the ideal for the such a dual sensor system.

Figure 2:
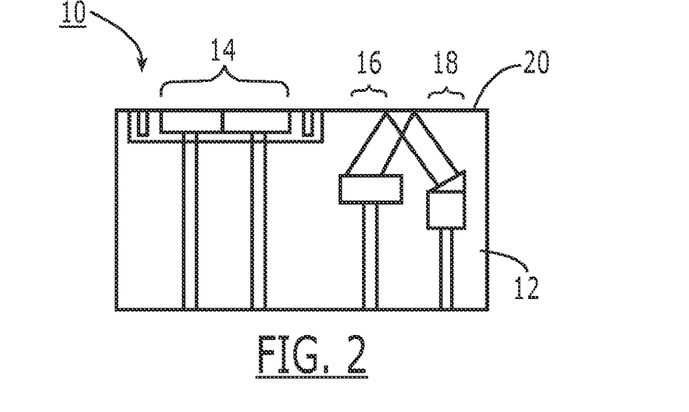
FIG. 2 is a cut-away side view of a portion of the hybrid electrical/optical fingerprint sensor structure illustrated in FIG. 1.

In accordance with the embodiment shown in FIG. 1, the secondary sensor array comprises an array of sensors 16 and associated light sources 18. FIG. 2 is a cut-away side view of the embodiment shown in FIG. 1. The actual arrangement and operation of the secondary sensor array can vary from embodiment to embodiment, and the following description is merely by way of example. The secondary sensor array may operate on the principle of total internal reflection, a technique known in the art. For example, light from light source array 18 is made incident on the fingerprint of a user placed on top surface 20. Peaks (or ridges) in the fingerprint will be in contact with surface 20, while valleys will not. At points where the fingerprint does not touch surface 20 (i.e., valleys) the light from source 18 will be internally reflected by surface 20 and captured by sensor 16, while at points where the fingerprint touches surface 20 (i.e., peaks), the light from source 18 will exit the body structure 12, or alternatively its reflective path within body structure 12 will be altered. Alternatively, the wavelength(s) of light from light source 18 may be selected such that it is reflected by sub-dermal tissue and captured by sensor 16, and thus used to measure attributes of a user's skin and/or tissue other than the fingerprint pattern itself. See, e.g., U.S. Pat. No. 7,147,153 which is incorporated herein by reference.

Figure 3:
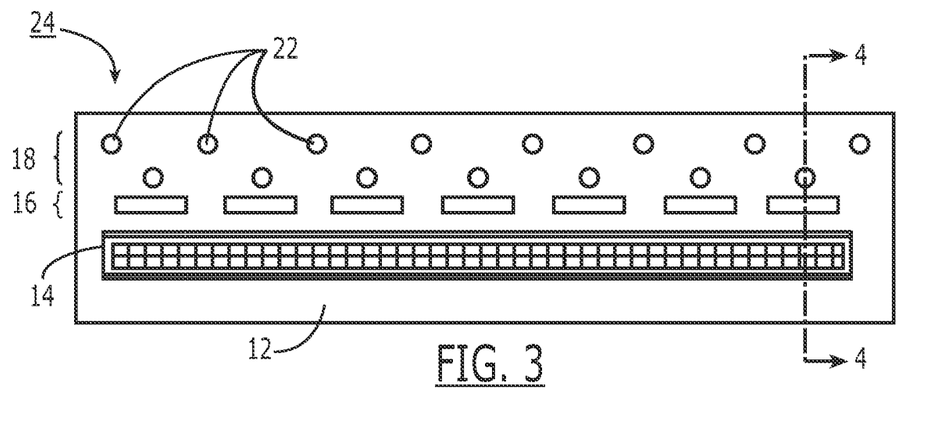
FIG. 3 is a plan view of a hybrid electrical/optical fingerprint sensor structure according to an alternate embodiment of the present invention.

Visible light is often absorbed by the skin or other tissue, making sensing of those wavelengths difficult. Accordingly, one embodiment of the present invention is provided with a secondary sensor light source which emits in the non-visible wavelengths, such infrared. However, light source array 18 may provide non-sensor source functionality and even an aesthetic purpose as well as being a light source for a sensing system. Accordingly, in an alternate embodiment of the present invention, the light source emits at one or more wavelengths of light visible to a user. The user may thus be provided cues to assist in the use of the sensor and feedback regarding successful or unsuccessful operation of the sensor. For example, the sensor may blink when an image is successfully acquired, or highlight with varying colors or intensity where or how fast a user should place and move a finger relative to the sensing device. The sensor may also be provided with a visual uniqueness (e.g., illumination color) to enhance marketing and permit distinguishing the source of the sensor from other manufacturers or products. Therefore, according to these embodiments of the present invention, the light sources forming array 18 emit at a desired visible wavelength, under control of a controller (not shown). Alternatively, in those cases in which secondary sensor array 16 requires non-visible light sources, optional supplemental light sources 22 may be interspersed in or placed proximate array 18, as illustrated in FIG. 3. Thus, the light emitting from light source array 18, and/or optional supplemental light sources 22 may be monochromatic, polychromatic, within and/or outside the visible spectrum, etc.

Figure 4:
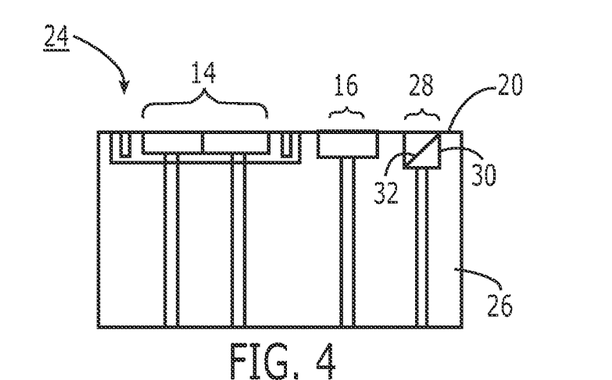
FIG. 4 is a cut-away side view of a portion of a hybrid electrical/optical fingerprint sensor according to the embodiment of the present invention shown in FIG. 3.

In the aforementioned embodiments, body structure 12 was transmissive at the wavelengths of emission of the light sources. However, with reference to FIG. 4, by mounting the secondary sensor array at the surface of the body structure, coplanar with the electronic sensor array 14, an opaque-material body structure 26 may be employed. In this embodiment, the secondary sensor array will operate on the principle of directly sensed reflection from the skin or tissue of the user, as the opaque body structure 26 will preclude internal transmission and reflection. The structure is similar to that previously described, but with optical sensor array 16 mounted to have its upper surface coplanar with the surface of electrical sensor array 14 on surface 20 of body structure 26. Each light source array 28 may optionally comprise two elements: a light source 30, and a lens 32 for directing the output of light source 30 so that reflections will be sensed by the sensors of array 16. Alternatively, light source 30 may be of a type, and positioned, such that a lens 23 is not required.

Figure 5:
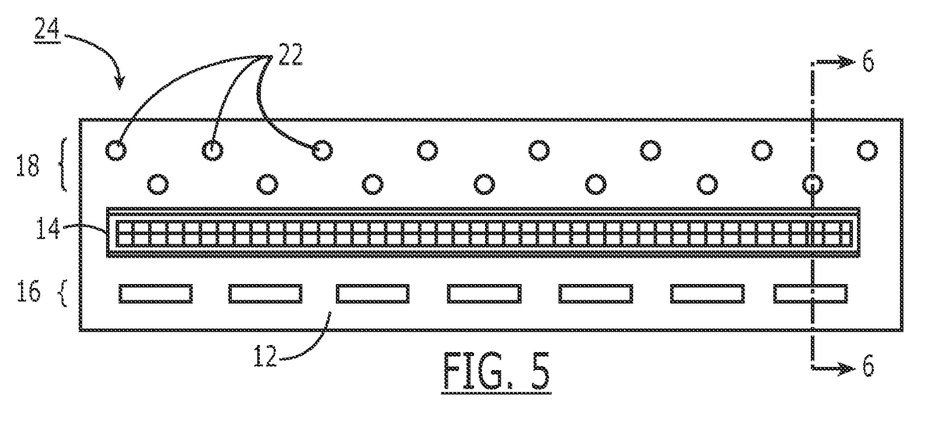
FIG. 5 is a plan view of a hybrid electrical/optical fingerprint sensor structure according to a further embodiment of the present invention.
Figure 6:
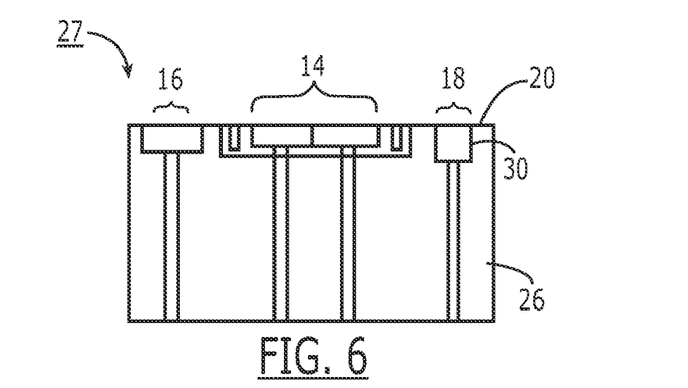
FIG. 6 is a cut-away side view of a portion of a hybrid electrical/optical fingerprint sensor according to the embodiment of the present invention shown in FIG. 5.

In a variation of the above described embodiment, as shown in FIGS. 5 and 6, the optical sensor array 16 and light source array 18 may be mounted on opposite sides of electrical sensor array 14. The location of the optical sensor array 16 and light source array 18 relative to the electrical sensor array is a matter of design choice.

Figure 7:
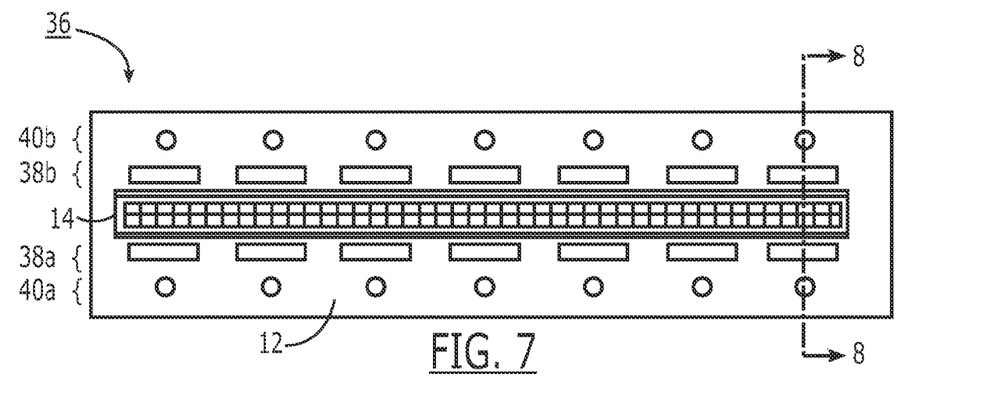
FIG. 7 is a plan view of a hybrid electrical/optical fingerprint sensor structure according to yet another embodiment of the present invention.
Figure 8:
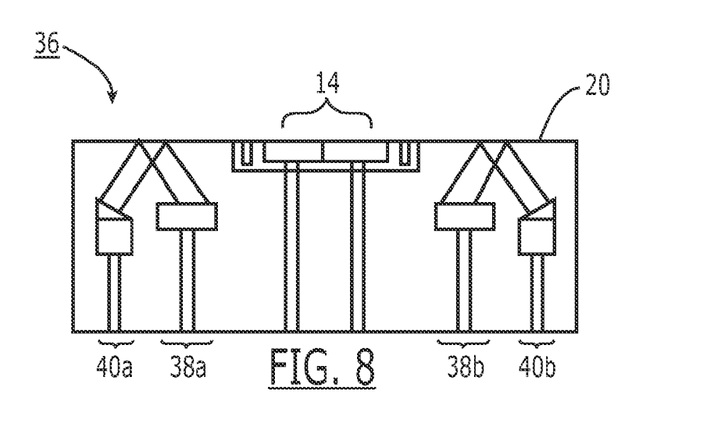
FIG. 8 is a cut-away side view of a portion of the hybrid electrical/optical fingerprint sensor structure according to the embodiment of the present invention illustrated in FIG. 7.

In still another embodiment of the present invention, illustrated in FIGS. 7 and 8, more than one secondary sensing array may be provided. In the example of FIGS. 7 and 8, first optical sensor array 38a and first light source array 40a are positioned opposite a second optical sensor array 38b and second light source array 40b, with electrical sensor array 14 disposed therebetween. The operation of the embodiment of FIGS. 7 and 8 is similar to that previously described, with the possible exception that additional data about the identity and validity of a fingerprint sensed by the system may be obtained. For example, the data from first optical sensor array 38*a* and second optical sensor array 38*b* may be combined to mathematically approximate the portion of the fingerprint being sensed by the electrical sensor array 14, approximating simultaneously sensing the same portion of the fingerprint by a multiplicity of different sensor devices.

Figure 9:
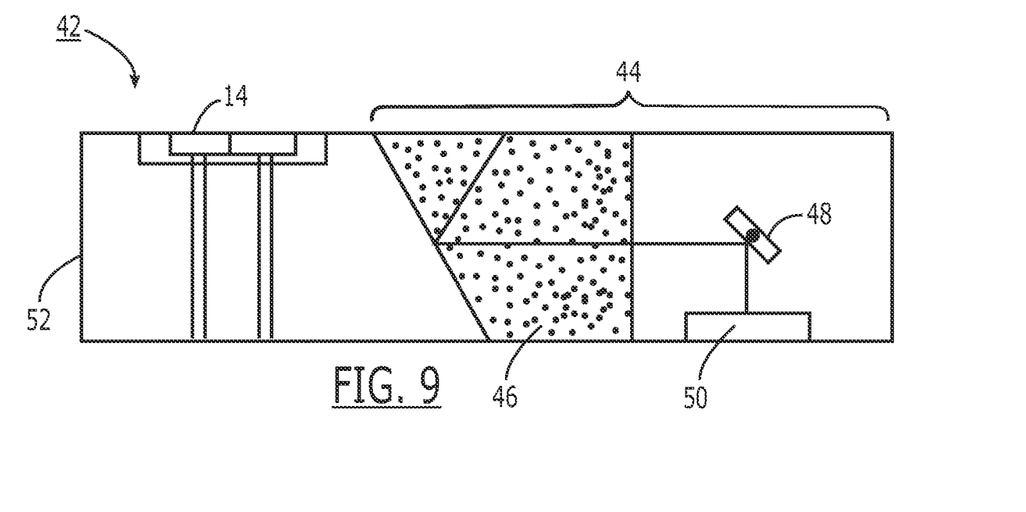
FIG. 9 is a cut-away side view of a portion of a hybrid electrical/optical fingerprint sensor according to an additional embodiment of the present invention.

One feature of the previously described embodiments is that the various sensors (and optional light sources) are integrated into a single substrate. This is particularly advantageous from manufacturing and overall size perspectives. However, it is within the spirit and scope of the present invention that one or more of the sensing devices forming the structure of the present invention be a discrete sensing device operating cooperatively with another discrete sensing device. One embodiment 42 of such a device is shown in FIG. 9. According to this embodiment, an electrical sensor array 14 is disposed in close proximity to an optical sensor assembly 44. Optical sensor assembly 44 may comprise a reflective prism 46 for obtaining an image of a fingerprint (or when illuminated, details of the skin and other tissue below the surface of the finger, as previously described), a scanning mirror 48 for imaging different portions of the fingerprint, and a sensor 50 for sensing the image of the fingerprint. Other arrangements of the various elements of the optical sensing assembly may also be employed, such as disclosed in U.S. Pat. No. 5,942,761 and U.S. Pat. No. 6,980,286, which are each incorporated herein by reference. While the aforementioned elements may be carried by a common mounting structure 52, various elements according to this embodiment are formed on discrete substrates and assembled onto mounting structure 52 as may be appropriate for specific applications.

Figure 10:
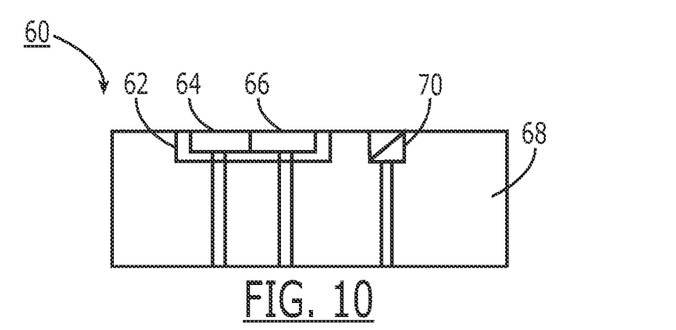
FIG. 10 is a cut-away side view of a portion of a hybrid electrical/optical fingerprint sensor according to an embodiment of the present invention which includes two or more different sensor types integrally formed on a single substrate.

As mentioned above, one feature of the present invention is the ability to form one or more of the different sensing apparatus integrally, on a single substrate, using common processing steps (that is, at least some of the processing steps used to form one device may also be used simultaneously to form the second device). For example, a capacitive and optical sensor may each be formed on crystalline silicon substrate using a number of common processing steps. Thus, with reference to FIG. 10, a structure 60 comprises a single sensor substrate 62 carrying two different sensors 64, 66 each operating on a different principal (e.g., capacitive and optical) may be disposed in a carrier body 68. Optionally, a light source 70 may also be disposed within carrier body 68. By forming the different sensor types integrally on a single substrate, the distance between the different sensor types is minimized.

Figure 11:
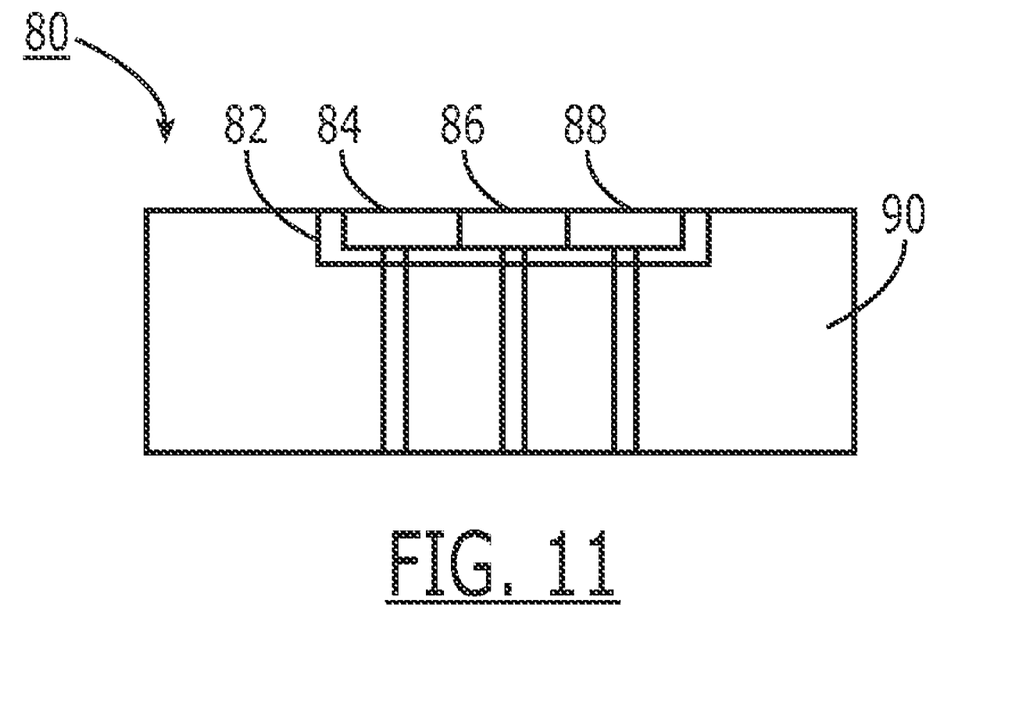
FIG. 11 is a cut-away side view of a portion of a hybrid electrical/optical fingerprint sensor according to an embodiment of the present invention which includes two or more different sensor types and one or more light sources integrally formed on a single substrate.

It is also known today to form solid-state light emitting devices, such as light emitting diodes, from material systems such as aluminum-gallium-indium, etc. Such a system may also be employed to form electrical and optical sensors, enabling the formation of a fully integrated multi-sensor and light source biometric identification system 80, illustrated in FIG. 11, in which a single substrate 82 having formed therein two different sensor types (e.g., capacitive and optical) 84, 86 and solid-state light source 88 is disposed within a carrier body 90. Again, by forming the different sensor types integrally on a single substrate, the distance between the different sensors is minimized.

While a plurality of preferred exemplary embodiments have been presented in the foregoing detailed description, it should be understood that a vast number of variations exist, and these preferred exemplary embodiments are merely representative examples, and are not intended to limit the scope, applicability or configuration of the invention in any way. For example, the embodiments described above employ one or more 1-dimensional electrical sensors (strip sensors) as the electrical sensor array. However, other electrical sensors can be used, such as a 2-dimensional sensor (area sensor), particularly when it is not crucial to sense the same part of the finger simultaneously or when minimizing size or cost is not a primary concern. Furthermore, the secondary sensor array has been described as an optical sensor array. However, any of a large number of other sensor types, such as thermal (e.g., U.S. Pat. No. 6,061,464, which is incorporated herein by reference), resistive (e.g., U.S. Pat. No. 5,864,296, which is incorporated herein by reference), pressure (e.g., U.S. Pat. No. 5,844,287, which is incorporated herein by reference), etc. may be employed. If fact, according to the present invention, the two sensor arrays may both be electrical, but of differing types so that the sensing function of one does not interfere with the sensing function of the other. Finally, reference has been made herein to the unique characteristics of fingerprints, and formation of a fingerprint sensor. However, other portions of a body also have unique characteristics, such as toes, etc., and the present invention may also be used for identification based on those other body portions. Therefore, the foregoing detailed description provides those of ordinary skill in the art with a convenient guide for implementation of the invention, and contemplates that various changes in the functions and arrangements of the described embodiments may be made without departing from the spirit and scope of the invention defined by the claims thereto.

What is claimed is:

1. A hybrid multi-sensor biometric identification device which senses biometric data associated with a user's finger, comprising:

an integrated circuit substrate;

a first sensor apparatus formed on said integrated circuit substrate for sensing characteristics, indicative of a fingerprint pattern, of the surface and/or structure of skin at or proximate the tip of the user's finger, said first sensor operating on the principle of sensing changes in the fringing field established between elements thereof due to variations in the fingerprint pattern of the user's finger;

an array of light sources integrally formed on said integrated circuit substrate, said array of light sources generally being at least as wide as the width of the user's finger, said light sources emitting at least in the visible light spectrum such that the output of said light sources may be used to give visual indications to the user relating to operation of the biometric identification device; and a second sensor apparatus formed on said integrated circuit substrate adjacent said array of light sources, of a type for sensing biometric data associated with said user's finger utilizing at least a selected wavelength of the light output by said array of light sources.

2. The hybrid multi-sensor biometric identification device of claim 1, wherein said first and second sensor apparatus are disposed for operation such that they may simultaneously sense nearly identical regions of the surface and/or structure of the skin.

3. The hybrid multi-sensor biometric identification device of claim 1, wherein said light source is polychromatic.

4. The hybrid multi-sensor biometric identification device of claim 3, wherein said second fingerprint sensor apparatus selectively senses in at least one wavelength band emitted by the light source.

5. The hybrid multi-sensor biometric identification device of claim 1, wherein said second sensor apparatus is capable of sensing characteristics of living human tissue, thereby permitting distinguishing between living human tissue and non-living and/or non-human material.

6. The hybrid multi-sensor biometric identification device of claim 1, wherein said first and second sensor apparatus are each formed on said integrated circuit substrate by common processing steps.

7. The hybrid multi-sensor biometric identification device of claim 1, wherein said substrate is crystalline silicon.

8. A hybrid multi-sensor biometric identification device which senses biometric data associated with a user's finger, comprising:
   a silicon substrate having integrally formed therein:
      a capacitive fingerprint sensor apparatus for sensing characteristics, indicative of a fingerprint pattern, of the surface and/or structure of a user's skin at or proximate the tip of the user's finger;
      an array of polychromatic light sources, said array generally being at least as wide as the width of the user's finger, said light sources emitting at least in the visible light spectrum such that the output of said light sources may be used to give visual indications to the user relating to operation of the biometric identification device;
      an optical fingerprint sensor apparatus for sensing characteristics of living human tissue utilizing at least a selected wavelength of the light output by said array of light sources, thereby permitting distinguishing between living human tissue and non-living and/or non-human material;
   wherein said optical fingerprint sensor is capable of sensing said selected wavelengths and further wherein said capacitive fingerprint sensor apparatus and said optical fingerprint sensor apparatus are disposed within said substrate for operation such that they may simultaneously sense nearly identical regions of the surface and/or structure of the skin.

* * * * *